United States Patent [19]
Nyman

[11] Patent Number: 5,392,791
[45] Date of Patent: Feb. 28, 1995

[54] CONTROLLABLE INTRACARDIAL ELECTRODE DEVICE

[75] Inventor: Per Nyman, Djursholm, Sweden

[73] Assignee: Siemens Elema AB, Solna, Sweden

[21] Appl. No.: 52,153

[22] Filed: Apr. 23, 1993

[30] Foreign Application Priority Data

Apr. 24, 1992 [SE] Sweden ............................. 92012954

[51] Int. Cl.⁶ ............................................ A61M 25/01
[52] U.S. Cl. ................................. 128/772; 604/280; 606/129
[58] Field of Search ............... 128/772, 899; 607/119, 607/122; 606/129; 604/280, 281

[56] References Cited

U.S. PATENT DOCUMENTS

| | | |
|---|---|---|
| 3,452,742 | 7/1969 | Muller .................................. 128/772 |
| 3,802,440 | 4/1974 | Salem et al. ........................ 128/772 |
| 4,136,703 | 1/1979 | Wittkampf . |
| 4,257,429 | 3/1981 | Dickhudt et al. . |
| 4,401,127 | 8/1983 | Littleford . |
| 4,402,328 | 9/1983 | Doring . |
| 5,095,915 | 3/1992 | Engelson .............................. 128/772 |
| 5,123,422 | 6/1992 | Charvin . |

FOREIGN PATENT DOCUMENTS

0377453  7/1990  European Pat. Off. ............ 128/772

*Primary Examiner*—William E. Kamm
*Assistant Examiner*—Kennedy J. Schaetzle
*Attorney, Agent, or Firm*—Hill, Steadman & Simpson

[57] ABSTRACT

A controllable electrode device for intracardial stimulation of the heart with an electrode cable includes an elongate, flexible conductor having an exterior covered with a layer of insulation and an interior forming a lumen for the introduction of an element for assisting in guiding the electrode device through a vein, and having an electrode head fitted at the conductor's distal end for stimulation of cardiac tissue. In order to achieve an electrode device with an electrode cable which is pliant and flexible, at least in its anterior section, to promote being guided through a vein, and which can be guided and shaped in the heart in a desired manner, a guide arrangement is provided which includes an elongate element having at least one groove running roughly perpendicularly to the longitudinal direction of the element and having a shape and depth enabling the element, and therefore the electrode cable, to bend at the groove when the element is subjected to pressure in its longitudinal direction.

11 Claims, 1 Drawing Sheet

CONTROLLABLE INTRACARDIAL ELECTRODE DEVICE

BACKGROUND OF THE INVENTION

1. Field of the Invention

The present invention relates to a controllable electrode device for intracardial stimulation of the heart of the type having an electrode cable containing an elongate, flexible conductor whose exterior is covered with a layer of insulation and whose interior forms a lumen for the introduction of a control element for bending the cable, and with an electrode head fitted at the conductor's distal end for stimulation of cardiac tissue.

2. Description of the Prior Art

It is of major importance for the electrode cable in an electrode device of the type described above to be pliant enough so it can, when introduced into the patient's heart via a vein, follow the course of the vein without damaging venous walls. In most instances, the electrode cable is introduced with the aid of a guidewire, inserted into the cable's lumen, made of a material having the stiffness still needed to advance the electrode cable through the vein. The stiffness of the electrode cable can thus be varied, depending on the guidewire's diameter and material. At difficult passages in which the electrode must bend considerably, the guidewire is often retracted a little so the distal end of the electrode cable has maximum pliancy. After passing such a passage, the guidewire is again pushed forward to the electrode cable's distal end (i.e., distal relative to a stimulation device to b3 connected at an opposite end) in order to advance this end into the atrium or ventricle of the heart until the electrode head bears against the heart wall for stimulation of the heart.

In U.S. Pat. No. 4,402,328, an electrode device of the above described type is disclosed having a J-shaped, precurved electrode cable whose electrode head is intended for insertion in the auricle of the atrium. When the electrode cable is introduced into the heart, the cable is straightened with a relatively stiff *stylet, which could cause complications in the passage of certain venous bends.

Another such electrode device is described in U.S. Pat. No. 4,136,703. In this electrode device, a relatively stiff tube, extending the length of the electrode cable, is inserted into the electrode cable's lumen. A J-shaped, precurved stylet, kept straight with the aid of the tube, is inserted into the tube. When the distal end of the cable is inside the heart, the tube is retracted, thereby exposing the stylet, which then shapes the distal end of the cable. An electrode cable of this kind is extremely stiff.

SUMMARY OF THE INVENTION

It is an object of the invention is to provide an electrode device, of the above-described type, with an electrode cable which is pliant and flexible, at least in its anterior part, which can be guided through a vein and moreover which can be guided and shaped in the heart in a desired manner.

The above object is achieved in accordance with the principles of the present invention in an electrode cable having an interior lumen in which a guide means is disposed, the guide means being formed by an elongate element with at least one track or groove running roughly perpendicularly to the longitudinal direction of the element, the groove having a shape and depth enabling the element, and therefore the electrode cable, to bend at the groove when the element is subject to pressure along its longitudinal direction. The elongate element may be a wire attached interiorly at the electrode cable's distal end and which is pressed longitudinally with the aid of a stylet. The wire is then manually subjected to a pressure which is governed by the curvature the electrode cable curvature needs to assume. In this manner, the electrode cable's distal end can be controlled in such a way that it is easily advanced through a vein on into the heart in which it can be shaped in a desired manner.

In a further embodiment of the invention the elongate element is equipped with a plurality of consecutive tracks forming a sawtooth profile section. This makes it possible to achieve gentle curvature of the element, and thus gentle curvature of the electrode cable.

In a simple embodiment of the invention the elongate element is a part of the stylet.

In another embodiment of the invention the elongate element is elastic so it reverts to its original shape when the pressure abates. This is an advantage when the electrode is being guided through a vein and when the electrode head must penetrate trabecular network tissue in the wall of the ventricle so as to obtain good fixation with the heart wall. In this type of introduction, the distal end of the electrode cable is alternately bent and extended, at the same time as the cable is rotated on its longitudinal axis.

According to another embodiment of the invention, the elongate element is made of a material enabling the body to retain its curvilinear shape when the pressure abates. This is an advantage if the electrode head is to be applied to the auricle of the atrium, in which case the electrode cable's distal end must therefore be J-shaped.

DESCRIPTION OF THE PREFERRED EMBODIMENTS

Figure 1:
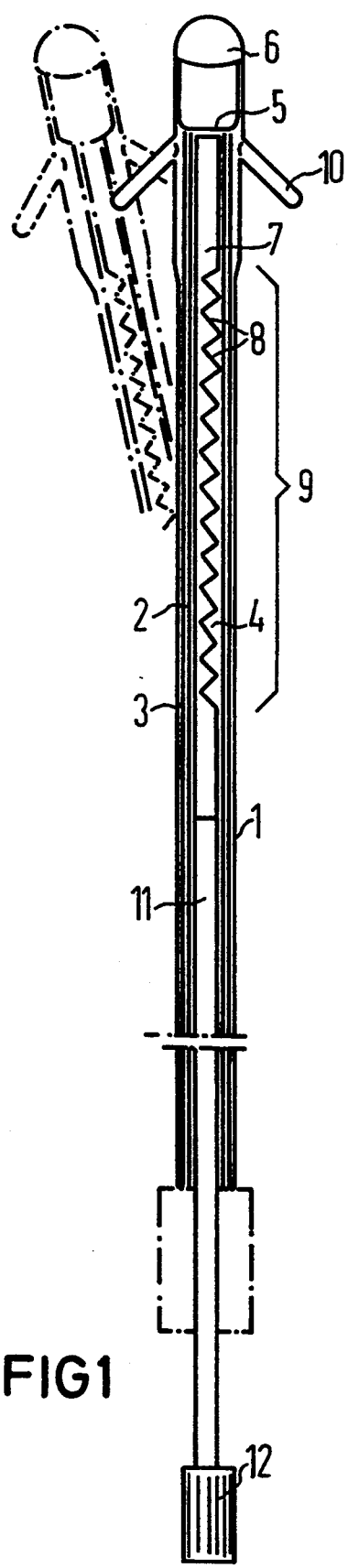
FIGS. 1 and 2 are side views of an electrode device constructed in accordance with the principles of the present invention.

FIG 1 shows an electrode device for intracardial stimulation of a heart constructed in accordance with the principles of the present invention. The electrode device, shown primarily in cross section, includes an electrode cable 1 containing an elongate conductor 2 whose exterior is covered with a layer of insulation 3 and whose interior forms a lumen 4. On the distal end 5 of the conductor 2, an electrode head 6 is mounted for stimulation of a patient's cardiac tissue. Fixing elements 10 for fixing the electrode head 6 are provided immediately behind the electrode head 6. An elongate element in the form of a wire 7, made of elastic material and supplied with a number of consecutive grooves 8 which form a sawtooth profile section 9, is inserted in the channel 4. The wire 7 with the sawtooth section 9 is at the electrode distal end of the cable 1. The tracks 8 may be V-shaped or U-shaped as best suits a particular introduction.

Figure 2:
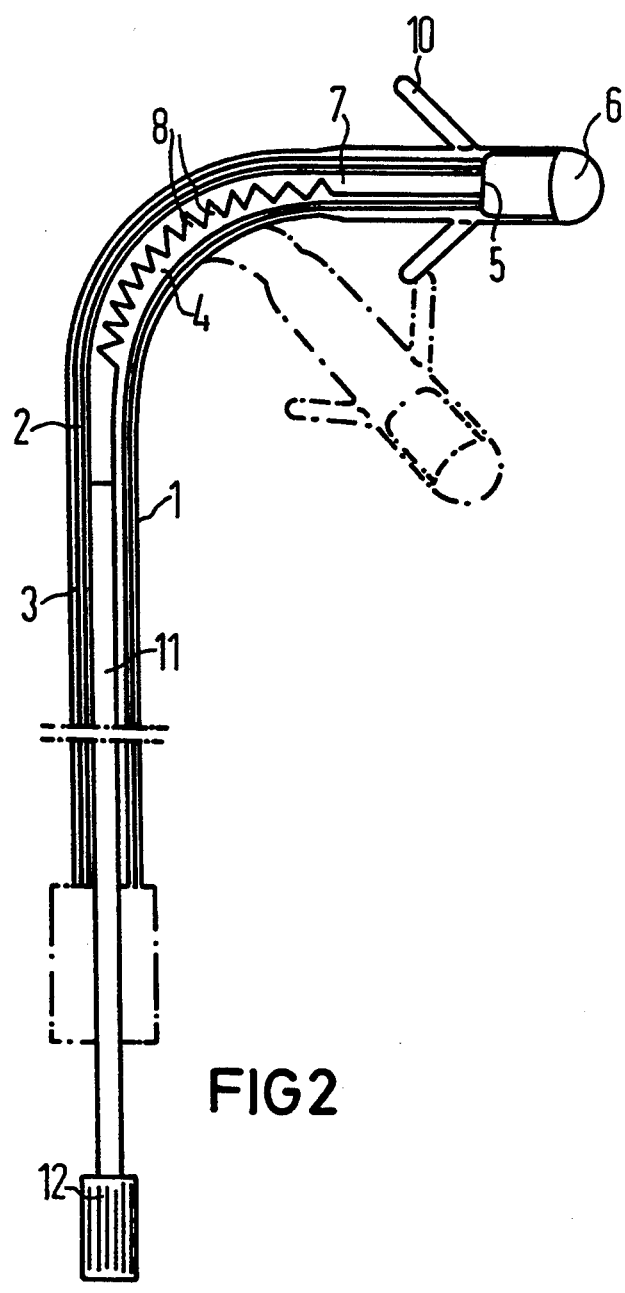

When the electrode cable 1 is introduced into a patient's vein, the operator is aided by a stylet 11 fed into the channel, making the very pliant electrode cable 1 somewhat stiffer. The stylet 11 is advanced in such a way that its terminal side presses against the terminal side of the wire 7. When the stylet 11 is pressed against the wire 7 the grooves 8 are deformed in such a way that the wire 7 is bent as shown in FIG. 2, whereupon the electrode cable 1 assumes the same curvature. When pressure is released, the wire 7, and therefore the electrode cable 1, reverts to its original position. Thus, the wire 7, with the aid of the stylet 11 can be subjected to a pressure which depends on the curvature the electrode cable 1 needs to assume. If the electrode cable 1 is rotated around its longitudinal axis, the cable 1 can be bent in the desired direction. One such direction is illustrated in FIG. 1 with a dashed rendition of the distal end of the electrode cable 1. If the wire 7, to advantage, is rotatably mounted in the channel 4, the wire can also be rotated around its longitudinal axis in order to achieve the above-described type of curvature of the electrode cable 1. In those instances wherein the wire 7 is to be rotated in the channel 4, the stylet 11 is immovably attached to the wire 7, or the wire 7 is a part of the stylet 11. Rotation of the stylet handle 12, the sawtooth part 9, and thus the distal end of the electrode cable 1 can be controlled in the desired manner. In the above described manner, the electrode cable 1 can be guided through a vein into the heart. When the distal end of the electrode cable 1 reaches the heart wall's trabecular network tissue, the electrode head 6, by means of alternating bending and extension of said electrode head 6, with possible concomitant rotation of the electrode cable around its longitudinal axis, penetrate the barrier and reach the heart wall. The fixing elements 10 prevent any dislocation of the electrode head 6.

If the electrode head 6 of the device is designed for placement in the auricle of the atrium, the wire is compressed in the above described manner, when the distal end of the electrode cable 1 reaches the atrium, so that a J-shape is imparted to the end, as illustrated by the dashed version of the distal end of the electrode cable 1 in FIG. 2. With such an electrode device, it may be advantageous to make the wire of a material which retains the curvilinear shape when pressure from the stylet 11 abates.

The wire 7 should be devised in such a way that the unloaded wire offers the conductor 2 minimal increase in the lateral stiffness or minimal wear on the conductor 2 surrounding the wire 7. Depending on the material used and the design of the grooves 8, use of the wire 7 provides a desired flexibility for the electrode cable's lateral stiffness so the distal end of the cable is soft and pliant and can be guided through a vein without exerting heavy pressure on the interior venous wall at a sharp bend in a vein. This minimizes the risk of penetration of the venous wall.

Although modifications and changes may be suggested by those skilled in the art, it is the intention of the inventor to embody within the patent warranted hereon all changes and modifications as reasonably and properly come within the scope of his contribution to the art.

I claim as my invention:

1. In a controllable electrode device for intracardial stimulation of the heart having an electrode cable containing an elongate, flexible conductor having an exterior completely covered with a layer of insulation and an interior forming a lumen for receiving a guide for selectively bending said electrode device during introduction of said electrode device through a vein, and an electrode head at the distal end of said conductor for stimulation of cardiac tissue, the improvement of said guide consisting of a single wire extending in said lumen in a longitudinal direction and having at least one groove running substantially perpendicularly to said longitudinal direction and having a shape and depth enabling the wire, and therefore the electrode cable, to bend at said groove when the said wire is subjected to pressure along said longitudinal direction.

2. A controllable electrode device as claimed in claim 1, wherein said wire has a plurality of consecutive grooves forming a sawtooth profile section.

3. A controllable electrode device as claimed in claim 2, wherein the sawtooth profile section is disposed at an anterior part of the electrode cable.

4. A controllable electrode device as claimed in claim 1 further comprising a stylet in said lumen and wherein said wire is a part of said stylet.

5. A controllable electrode device as claimed in claim 1 wherein said grooves are V-shaped.

6. A controllable electrode device as claimed in claim 1 wherein said grooves are U-shaped.

7. A controllable electrode device as claimed in claim 1 wherein said wire consists of elastic material, so that said wire reverts to an unbent shape when said pressure abates.

8. A controllable electrode device as claimed in claim 1 wherein said wire consists of material enabling said wire to retain said bend when said pressure abates.

9. A controllable electrode device as claimed in claim 1 wherein said wire is rotatably mounted in said electrode cable.

10. A method for guiding an electrode device through a vein for placement in a heart for intracardial stimulation of the heart, said method comprising the steps of:
    creating a lumen in an interior of a flexible conductor having an exterior completely covered with a layer of insulation and terminating at a distal end in an electrode head for stimulating cardiac tissue;
    providing a single wire terminating in a guide section and grooving said guide section with at least one groove running substantially perpendicularly to a longitudinal direction of said wire;
    inserting said wire in said lumen and guiding said electrode device through said vein and into said heart by subjecting said wire to pressure along said longitudinal direction, and selecting a shape and depth for said groove for permitting said conductor to bend to substantially follow curvatures in said vein and in said heart.

11. A method as claimed in claim 10 comprising the additional step of varying the pressure exerted on said wire for varying the curvature of said conductor as said conductor passes through said vein.

* * * * *